Figures 1, 2:
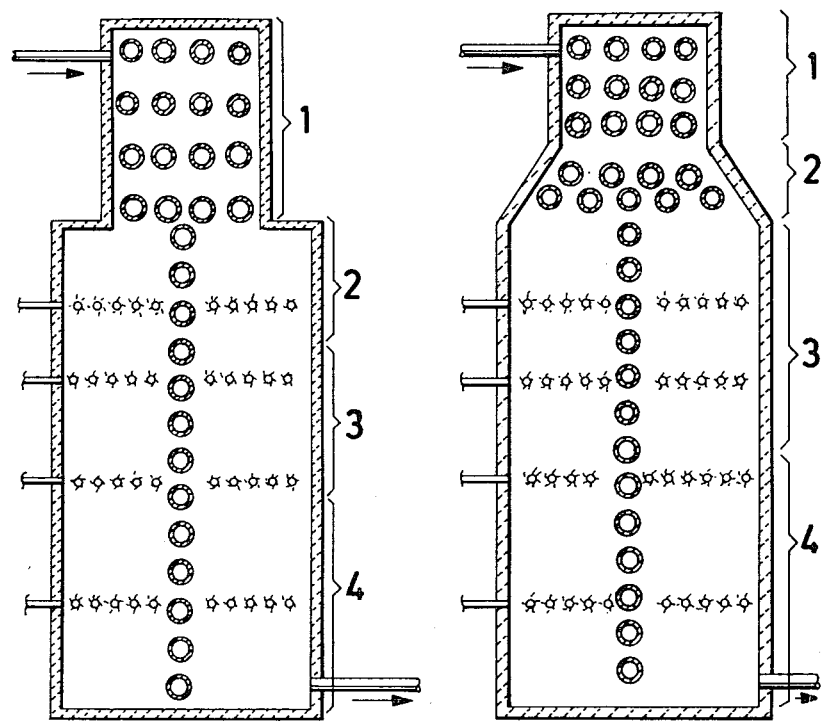

United States Patent [19]

Riedl et al.

[11] 4,225,520

[45] Sep. 30, 1980

[54] PROCESS FOR THE MANUFACTURE OF VINYL CHLORIDE

[75] Inventors: Josef Riedl; Walter Fröhlich, both of Burgkirchen; Erich Mittermaier, Tüssling, all of Fed. Rep. of Germany

[73] Assignee: Hoechst Aktiengesellschaft, Frankfurt am Main, Fed. Rep. of Germany

[21] Appl. No.: 728,715

[22] Filed: Oct. 1, 1976

Related U.S. Application Data

[63] Continuation of Ser. No. 564,038, Apr. 1, 1975, abandoned.

[30] Foreign Application Priority Data

Apr. 6, 1974 [DE] Fed. Rep. of Germany ....... 2416786

[51] Int. Cl.² ............................................ C07C 21/02
[52] U.S. Cl. ............................................... 260/656 R
[58] Field of Search .......................... 260/656 R, 652 P

[56] References Cited

U.S. PATENT DOCUMENTS

| | | | |
|---|---|---|---|
| 2,081,322 | 5/1937 | Carney | 260/660 |
| 2,748,176 | 5/1956 | Morris | 260/652 P |
| 3,843,736 | 10/1974 | Rechmeier et al. | 260/656 R |

FOREIGN PATENT DOCUMENTS

| | | | |
|---|---|---|---|
| 586326 | 11/1959 | Canada | 260/654 D |
| 938824 | 10/1963 | United Kingdom | 260/656 R |
| 1186742 | 4/1970 | United Kingdom | 260/660 |

*Primary Examiner*—Delbert E. Gantz
*Assistant Examiner*—Joseph A. Boska
*Attorney, Agent, or Firm*—Connolly and Hutz

[57] ABSTRACT

Vinyl chloride is produced by pyrolytic decomposition of 1,2-dichloroethane in a furnace with coiled up reaction tube having an internal diameter of from 12 to 16 cm. The dichloroethane is vaporized completely in the convection zone of the pyrolytic furnace, different amounts of heat are supplied to the different zones of the reaction tube and, after decomposition in the working up of the reaction products, the low-boiling constitutents are treated with chlorine and separated together with the high-boiling constituents.

4 Claims, 3 Drawing Figures

PROCESS FOR THE MANUFACTURE OF VINYL CHLORIDE

CROSS REFERENCE TO RELATION APPLICATIONS

This application is a continuation of Ser. No. 564,038, filed Apr. 1, 1975 by the same inventors, now abandoned.

The present invention relates to a process for the manufacture of vinyl chloride by pyrolytic decomposition of 1,2-dichloroethane in a furnace containing a coiled up cracking tube having an inner diameter of from 12 to 16 cm, wherein the dichloroethane is completely vaporized in the convection zone of the furnace, in the cracking zone the coiled tube is supplied with different amounts of heat and after cracking in the working up of the reaction products chlorine is fed to the column in which the high boiling constituents are separated, in the absence of a catalyst.

To carry out the pyrolysis of dichloroethane to yield vinyl chloride and hydrogen chloride without the aid of a catalyst several methods are known in industry which differ in the pressure under which the pyrolysis is carried out. There are known the so-called low pressure pyrolysis under an excess pressure of about 10 atmospheres and a pyrolysis under higher pressure of from 15 to 40 atmospheres gauge (cf. British Pat. No. 938,824).

In the process under the higher pressure the pyrolysis is influenced by the temperature and the conversion rate. The higher these parameters, the greater the proportion of unwanted by-products formed, for example low-boiling, saturated and unsaturated hydrocarbons such as butadiene-1,3, acetylene, 2-chloro-butadiene-1,3, 1,1-dichloroethylene, 1,1-dichloroethane, chloroform, 1,1,2-trichloroethylene, as well as aromatic hydrocarbons, for example benzene. After partial separation of the by-products, especially of butadiene-1,3, the 1,2-dichloroethane which has not been decomposed in one passage is recycled to the pyrolysis together with fresh 1,2-dichloroethane.

In industry it is absolutely necessary to reduce the proportion of the aforesaid by-products in the recycled unreacted dichloro-ethane in order to avoid a rapid clogging of the pyrolytic furnace with soot and coke. Up to now, this is achieved by distillation, which necessarily involves a loss of 1,2-dichloroethane.

According to British Pat. No. 938,824 dichloroethane is pyrolytically decomposed to yield vinyl chloride and hydrogen chloride at a conversion rate of 50 to 70% in a tube coiled upon itself and having an internal diameter of from 2.42 cm to 8.5 cm, at a temperature in the range of from 480° to 540° C. The pressure which is adjusted at the outlet side of the furnace is in the range of from 20 to 38 atmospheres gauge. The hot gases leaving the furnace are quenched and passed through 4 series-connected columns in which hydrogen chloride, vinyl chloride and small proportions of by-products are separated and unreacted dichloroethane is recovered. In the combined system, generally used nowadays, the hydrogen chloride obtained is reacted with ethylene and atmospheric oxygen in the so-called oxichlorination to yield again dichloroethane. Vinyl chloride is the starting material for making polyvinyl chloride. The low-boiling by-products are burned or transformed into other substances by chemical reaction. The unreacted dichloroethane is recycled into the pyrolysis.

A drawback of the described process resides in that after a period of at most 6 to 8 weeks the furnace has to be shut down because of soot and carbon deposits, the columns have to be cleaned two to three times a year and the removal of the unwanted lowboilers requires a considerable expenditure pertaining to apparatus and energy.

It has now been found that the proportion of unwanted by-products can be reduced and the operating time of the pyrolytic furnace can be considerably prolonged by using a reaction tube coiled upon itself and having a diameter of from 12 to 16 cm, supplying the upper part of the furnace with about two times as much heat as the lower part and, for better separating the reaction products during the distillation of the unreacted dichloroethane by reacting the unsaturated lowboilers formed in the pyrolysis with gaseous chlorine in the highboiler column. Hence, during to the distillative separation of the high-boiling constituents from dichloroethane, the unsaturated low-boiling constituents contained in the unreacted dichloroethane are transformed by means of gaseous chlorine into higher boiling chlorination products which are separated as highboilers before the dichloroethane is subjected to pyrolysis. The reaction with gaseous chlorine is carried out in the absence of a catalyst and the chlorine amount is preferably chosen in such a manner that only 20 to 80% of the double bonds present are saturated. The aforesaid measures permit to double the operating time of the pyrolysis furnace and of the columns and a lowboiler column requiring much energy can be dispensed with.

The enlargement of the internal diameter of the reaction tube involved a considerable technical risk as it was uncertain whether the longer residence time of the gases in the hot tube resulting therefrom would bring about a decomposition of dichloro-ethane, vinyl chloride and the aforesaid by-products into smaller fragments with increased deposition of carbonaceous products in the form of soot and coke in the reaction tube. Acetylene, probably a decomposition product of vinyl chloride, has been detected in the cracked gases for a long time.

Surprisingly, the enlargement of the tube diameter had a positive effect. Due to the longer residence time of the gases in the hot zone of the furnace, the decomposition temperature could be lowered by about 40° to 50° C. with respect to a reaction in small diameter tubes. The pyrolysis in the larger tube according to the invention is generally carried out at a temperature in the range 480° to 510° C. and consequently, depending on the temperature in each specific case, the proportion of unwanted by-products can be diminished by 30 to 80%. By this measure the discharge of soot and coke from the furnace decreased to such an extent that in the columns connected at the outlet side of the furnace no deposit could be observed in the separating or rectifying section of the columns after an operating time of 4 months.

The following table illustrates the reduction of the content of 2-chlorobutadiene-1,3 (chloroprene) in dependence on the cracking temperature. 2-Chlorobutadiene-1,3 is considered the principle coke forming constituent.

TABLE

| pyrolysis temperature °C. | chloroprene ppm | internal tube diameter cm |
|---|---|---|
| 550 | 870 | 6.23 |

TABLE-continued

| pyrolysis temperature °C. | chloroprene ppm | internal tube diameter cm |
| --- | --- | --- |
| 528 | 580 | 13.42 |
| 510 | 230 | 13.42 |

The tendency is similar with other by-products, for example acetylene, in dependency on the pyrolysis temperature.

With the use of a reaction tube of larger diameter the heating method practiced up to now was no longer possible. While with furnaces of small dimensions the required amount of heat is mainly introduced in the lower part of the radiation zone, in large furnaces the hot part of the radiation zone must be relieved from heat as far as possible for technological reasons and for safety and therefore the zone in which the dichloroethane is superheated supplied with larger amounts of flue gas.

Figure 3:
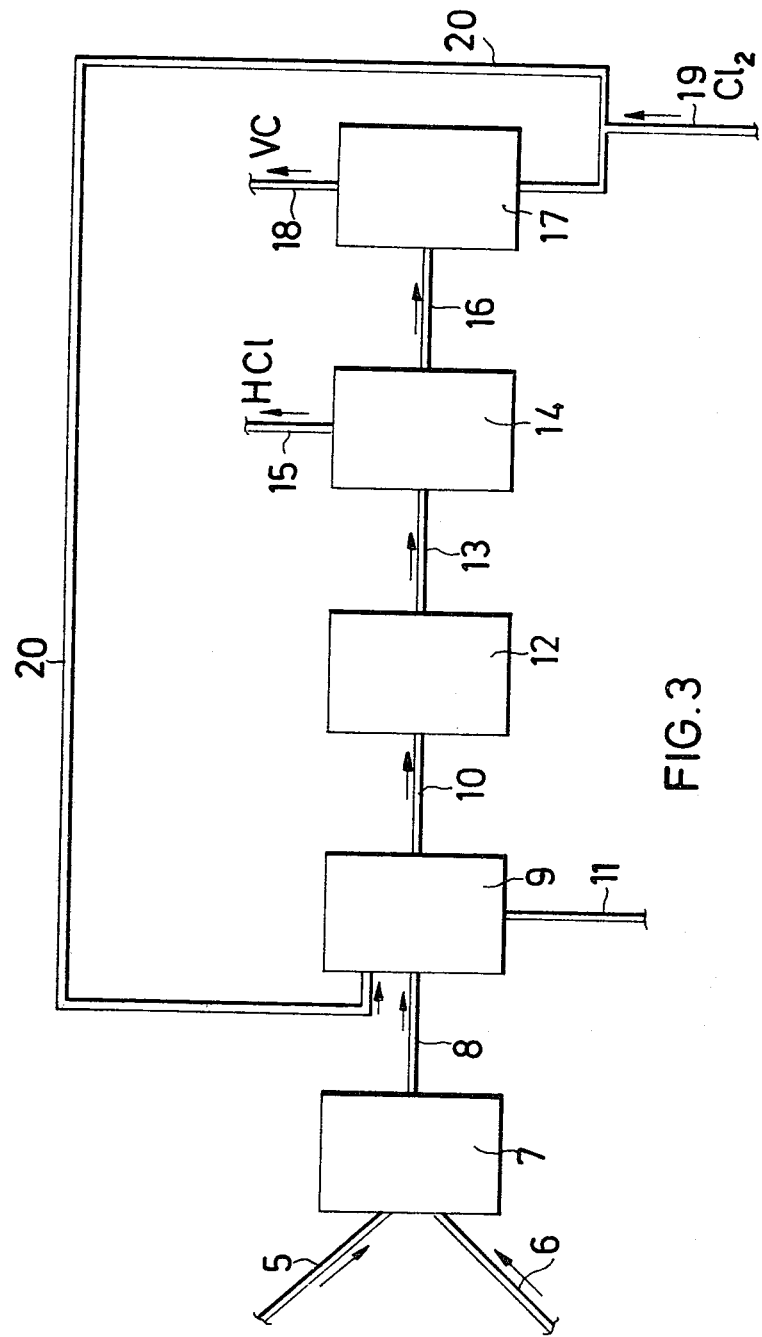

The invention will now be described in further detail with reference to the accompanying drawing, of which FIG. 1 shows a furnace of conventional construction FIG. 2 is a representation of a furnace of novel construction and FIG. 3 is a flow scheme of the vinyl chloride production.

As shown in FIGS. 1 and 2, a pyrolysis furnace 12 for dichloro-ethane is generally subdivided into four zones, i.e.

(1) the convection zone in which the liquid dichloroethane is preheated,
(2) the vaporization zone of dichloroethane which is especially critical with respect to carbonization,
(3) the heating zone of the dichloroethane vapors,
(4) the cracking zone.

The dichloroethane should preferably be vaporized at temperatures of the tube wall which are as close as possible to the boiling point of dichloroethane in order to keep as low as possible the coke deposit in the respective part of the furnace.

In furnaces of older construction the zone of total vaporization, i.e. the vaporization zone 2 is within the radius of influence of the upper row of burners (cf. FIG. 1) and, therefore, attempts were made thermally to relieve the upper rows of burners and to feed the lower rows with a higher amount of flue gas, the proportion of flue gas of the two lower to the two upper rows varying between 1.1 to 1.5:1.

In furnaces of improved construction (FIG. 2) the vaporization zone 2 is moved from the zone of influence of the upper rows of burners, where the heat is transmitted to the wall of reaction tube 21 by radiation and convection, to the colder upper part of the furnace nearer to the convection zone 1, where the heat is transmitted to the tube wall by convection only. It has been ascertained that a furnace of the novel construction cannot be operated with the same distribution of flue gas (higher thermal load of the lower rows of burners) as a furnace of the older construction. When the heat was distributed in known manner the tube in the decomposition zone of the furnace was seriously damaged after a short period of time. This detrimental effect could only be eliminated by a decisive modification of the distribution of flue gas over the rows of burners.

The process according to the invention is carried out in a furnace of the novel construction.

In contradistinction to a conventional furnace heating, the two lower rows of burners had to be supplied with a smaller amount of heat while the upper range had to be loaded with about twice the amount of heat; the conditions being approximately as follows: with a ratio of heating of the two upper rows to the two lower rows of burners of 1.7:1 the tube wall in the decomposition zone of the furnace is damaged. Damage becomes more frequent towards a ratio of 1:1. On the other hand, the upper rows of burners should not be loaded with too high an amount of heat, because this would lead to rapid carbonization in the respective zone. With a ratio of flue gas of 2.4:1, the tube in the vaporization zone of the dichloroethane is clogged by carbonization within a few day, perceptible by a rapid increase of the tube wall temperature and of the furnace pressure. Optimum conditions are reached with a ratio of approximately 2:1 which permit a period of operation of the furnace of up to 4 months. In general, the two upper rows of burners will be supplied with 1.7 to 2.3 times the amount of heat fed to the lower rows of burners by metering the flue gas accordingly. The preferred heating ratio ranges from 1.8:1 to 2.2:1.

The aforesaid measures, which belong to the technological field and which reduce the formation of coke and decomposition by-products by 30 to 40%, are complemented and intensified by an additional chemical reaction. By treating with gaseous chlorine the by-products of the pyrolytic decomposition, leaving the sump of the vinyl chloride column together with the unreacted dichloroethane and recycled together with the latter into the highboiler column, the chloroprene (2-chlorobutadiene) content of the recycled dichloroethane can be diminished by a further 100 to 200 ppm without using a catalyst.

The chlorination reaction in the vinyl chloride production will now be described in further detail with reference to the accompanying flow scheme (FIG. 3).

The dichloroethane currents 5 and 6 moist with water from the direct chlorination and oxichlorination are dried in dehydrating column 7 by distilling off the azeotrope dichloroethane/water (boiling point 71.6° C. under 760 mm Hg). The dried dichloro-ethane is passed through conduit 8 into column 9 where it is freed of high-boiling constituents together with the dichloroethane recycled through conduit 20. The highboilers are removed through conduit 11. After the distillative purification the 1,2-dichloroethane is transferred through conduit 10 into reactor 12 where the pyrolytic decomposition takes place. The decomposition products are passed through conduit 13 into column 14 where hydrogen chloride is separated and removed through conduit 15. The mixture freed of hydrogen chloride is passed over conduit 16 into column 17 in which vinyl chloride is separated and discharged through conduit 18. Unreacted dichloroethane is recovered as sump product of column 17 and recycled into highboiler column 9 over conduit 20.

After partial separation of the low and high boiling constituents formed in the decomposition reaction it is used again for pyrolysis. To improve the removal of lowboilers chlorine is charged into highboiler column 9 through conduits 19 and 20 in an amount such that no chlorine can be detected in the distillate of the highboiler column. By the addition of chlorine the low-boiling constituents are transformed into chlorinated compounds having a higher boiling point than dichloroethane which are discharged from the sump of highboiler column 9 through conduit 11.

The following example illustrates the invention.

EXAMPLE 1,087.8 tons a day 1,2-dichloroethane were charged into a pyrolytic furnace with a coiled up reaction tube having an internal diameter of 132.4 mm in which 50.49% of the dichloroethane were decomposed. The furnace had a construction as shown in FIG. 2 and was provided with 4 rows of burners. The heat supply for the upper and lower rows was adjusted in a ratio of 2.1:1, i.e. the two upper rows were fed with 2.1 times as much heat as the two lower rows by a corresponding supply of flue gas. The decomposition temperature amounted to 510° C. The hot gases were quenched and separated by distillation into hydrogen chloride and vinyl chloride in two series-connected distilling columns from which hydrogen chloride and vinyl chloride were obtained as head products. The sump product of the vinyl chloride column containing unreacted dichloroethane was recycled together with 570 kg chlorine per day to the highboiler column preceding the pyrolytic furnace. At the same measure as dichloroethane was consumed in the decomposition reaction fresh dichloroethane was charged into the highboiler column together with the unreacted recycled dichloroethane. The head product of the highboiler column used as starting material for the decomposition had the following composition:

0.007% by weight of—vinyl chloride
0.005% by weight of—ethyl chloride
0.016% by weight of—1,1-dichloroethylene
0.024% by weight of—chloroprene
0.055% by weight of—1,1-dichloroethane
0.010% by weight of—carbon tetrachloride
0.551% by weight of—benzene
0.042% by weight of—chloroform
0.083% by weight of—1,1,1-trichloroethylene
99.141% by weight of—1,2-dichloroethane
0.005% by weight of—tetrachloroethylene
0.002% by weight of—ethylenechlorohydrin
0.059% by weight of—unknown constituents The pyrolytic furnace was operated for 4 months. Thereafter it was shut down for removing carbonaceous deposits. As compared therewith, a pyrolytic furnace in which the reaction tube had an internal diameter of 62.5 mm could be operated for at most 2 months.

What is claimed is:

1. In the process for the manufacture of vinyl chloride by pyrolytic decomposition of 1,2-dichloroethane in a furnace with a coiled up reaction tube, the furnace having a convection, a vaporization, a heating and a cracking zone from top to bottom and having upper and lower rows of burners, separating high-boiling constituents from 1,2-dichloroethane in a column preceding the furnace, passing the 1,2-dichloroethane through the reaction tube from top to bottom both the convection and the vaporizing zones being above the upper rows of burners carrying out the pyrolysis at a temperature of 480° C. to 510° C., separating hydrogen chloride and subsequently vinyl chloride from the cracked gas by distillation, recycling the sump product of the vinyl chloride separation to the column preceding the furnace while adding gaseous chlorine in the absence of a catalyst to the recycled sump product, the improvement which comprises using a reaction tube having an internal diameter of from 12 to 16 cm, and supplying through the upper rows of burners an amount of heat that is 1.8 to 2.2 times the amount of heat supplied through the lower rows of burners whereby rapid clogging by carbonization is prevented and operating periods are prolonged.

2. The process as set forth in claim 1, wherein the unsaturated by-products formed in the pyrolysis are transformed into chlorination products by treating them with gaseous chlorine.

3. The process of claim 2, wherein the unsaturated by-products having double bonds are treated with 20 to 80% of the stoichiometrically required amount of gaseous chlorine required to saturate all of the bonds present in the by-products.

4. In the process for the manufacture of vinyl chloride by pyrolytic decomposition of 1,2-dichloroethane in a furnace with a coiled up reaction tube, the furnace having a convection, a vaporization, a heating and a cracking zones from top to bottom and having a plurality of burner rows from top to bottom, both the convection zone and the vaporization zone being above the top row of burners and both the heating zone and the cracking zone being in that part of the furnace where the burner rows are situated, separating high-boiling constituents from 1,2-dichloroethane in a column preceding the furnace, passing the 1,2-dichloroethane through the reaction tube from top to bottom, carrying out the pyrolysis at a temperature of 480° to 510°, separating hydrogen chloride and subsequently vinyl chloride from the cracked gas by distillation, recycling the sump product of the vinyl chloride separation to the column preceding the furnace while adding gaseous chlorine in the absence of a catalyst to the recycled sump product, the improvement which comprises using a reaction tube having an internal diameter of from 12 to 16 cm, and supplying through the rows of burners in the heating zone an amount of heat that is 1.8 to 2.2 times the amount of heat supplied through the rows of burners in the cracking zone whereby rapdi clogging by carbonization is prevented and operating periods are prolonged.

* * * * *